United States Patent [19]

Robinson et al.

[11] 3,995,213

[45] Nov. 30, 1976

[54] SURFACE IMPEDANCE TESTER

[75] Inventors: Wesley A. Robinson, El Segundo; Peter J. Madle, Torrance, both of Calif.

[73] Assignee: The United States of America as represented by the Secretary of the Air Force, Washington, D.C.

[22] Filed: Oct. 2, 1975

[21] Appl. No.: 619,147

[52] U.S. Cl. ................................. 324/64; 324/34 R
[51] Int. Cl.$^2$ .......................................... G01R 27/14
[58] Field of Search ...................... 324/64, 62, 34 R

[56] References Cited
UNITED STATES PATENTS

| | | | |
|---|---|---|---|
| 2,735,754 | 2/1956 | Dravnieks | 324/64 X |
| 2,828,467 | 3/1958 | Stauffer | 324/64 X |
| 3,456,186 | 7/1969 | Bush et al. | 324/64 |
| 3,464,007 | 8/1969 | Williams | 324/64 |
| 3,611,125 | 10/1971 | Sharon et al. | 324/64 |
| 3,636,441 | 1/1972 | Fujimura | 324/64 |
| 3,721,897 | 3/1973 | Edling | 324/64 |

FOREIGN PATENTS OR APPLICATIONS 1,048,553  11/1966  United Kingdom ................... 324/64

*Primary Examiner*—Stanley T. Krawczewicz
*Attorney, Agent, or Firm*—Joseph E. Rusz; Robert Kern Duncan

[57] ABSTRACT

The permeability and resistivity of metal sheets including those installed in enclosing structures, are nondestructively determined by injecting a unit-step pulse of current into an exposed surface of the sheet and measuring the surface voltage gradient between a pair of contacts located between the current injection contacts. The permeability and resistivity of the metal determines the rate of diffusion of current into the surface and therefore the rate of decrease of this surface voltage gradient. At steady-state the current density will be uniform throughout the thickness of the sheet resulting in the surface voltage gradient stabilizing at a value depending on the resistivity and thickness of the metal.

1 Claim, 6 Drawing Figures

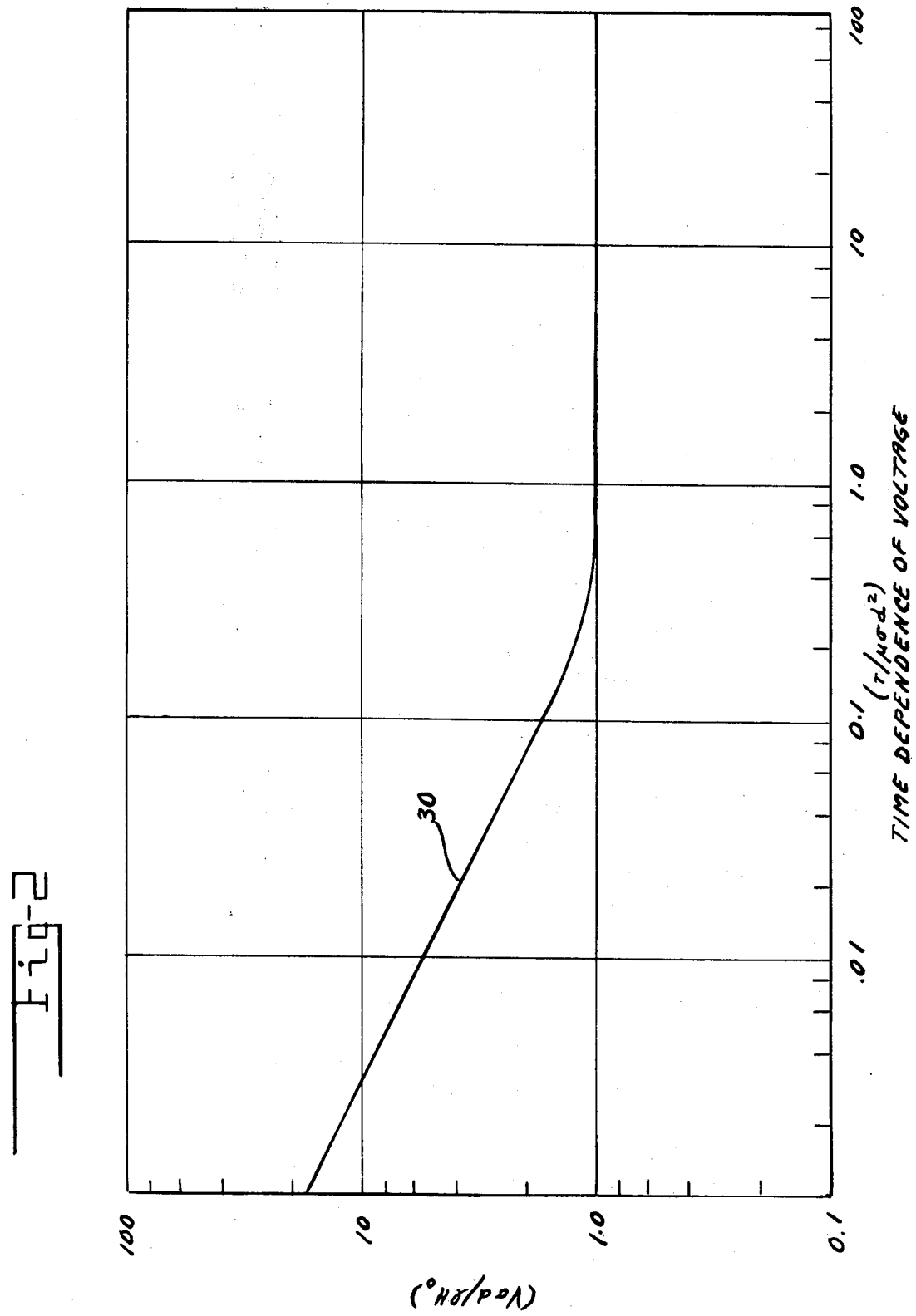

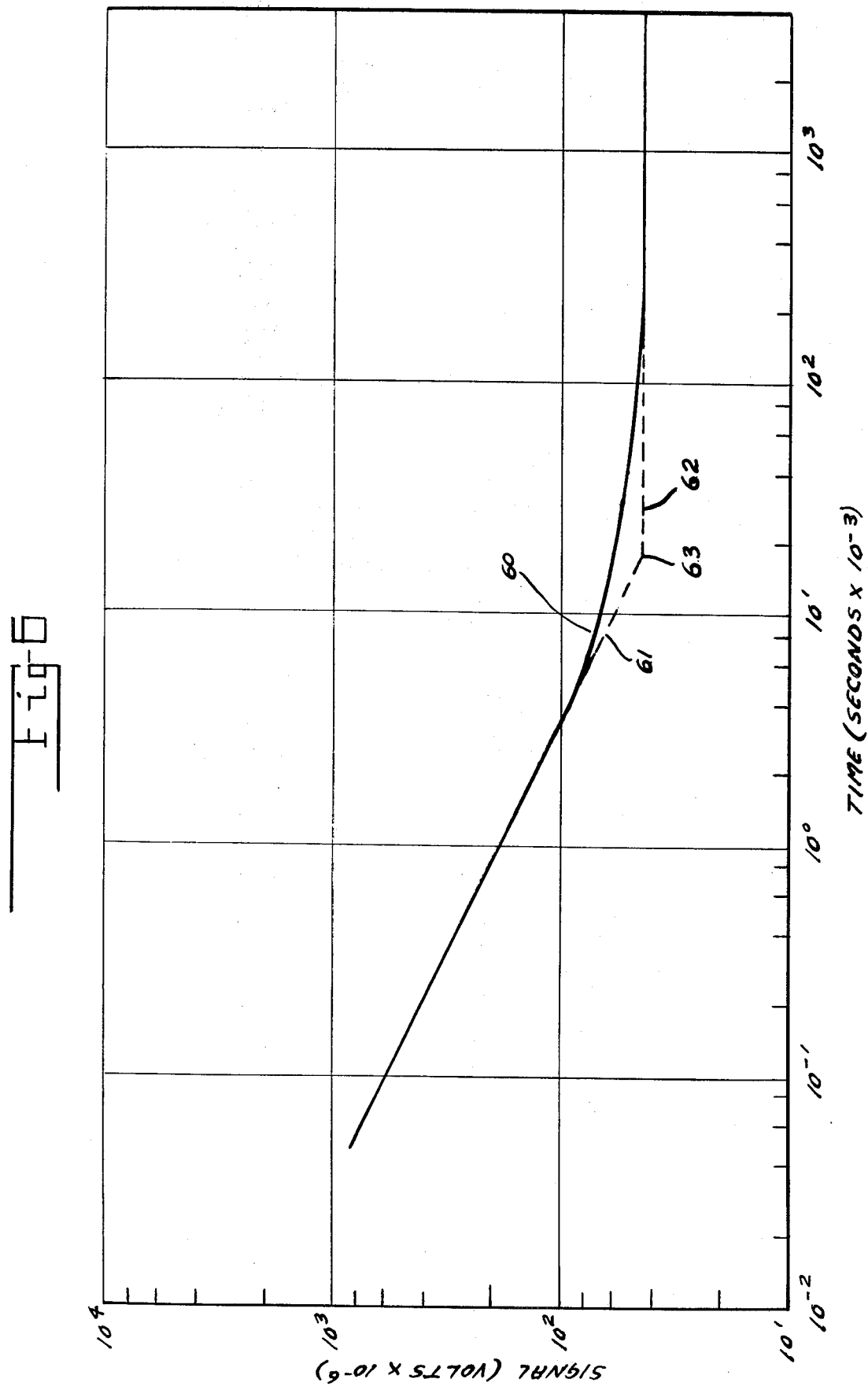

SURFACE IMPEDANCE TESTER

RIGHTS OF THE GOVERNMENT

The invention described herein may be manufactured and used by or for the Government of the United States for all governmental purposes without the payment of any royalty.

BACKGROUND OF THE INVENTION

The field of the invention is in the art of measuring nondestructively the permeability and resistivity of metal sheets.

Many buildings use steel as a magnetic shielding material. The magnetic properties of the steel are an important parameter in determining the quality of the shield. Frequently it is desired to use a previously constructed steel structure as a magnetically shielded enclosure and data on the material used is not available. Also, it is desirable to verify the shielding capabilities of newly constructed structures. The usual technique is to take a sample, i.e., cut it out of the existing structure, and run a B-H curve of the sample. This impairs the shield and frequently the properties of the sample are altered in the removing process and the measurements obtained therefrom are not truly indicative of the sheet from which it was removed.

Typical examples of the current state of the art are exemplified by U.S. Pat. Nos. 2,659,857 to patentee C. A. Anderson; 2,828,467 to patentee L. H. Stauffer; 3,611,125 to patentees Meyer Press et al; and 3,646,436 to patentees J. Y. Chan et al.

SUMMARY OF THE INVENTION

The method and apparatus for measuring, nondestructively, and without physical alternating, the impedance and obtaining both the inductive and resistive components thereof and therefore the permeability of in-place metallic structures is disclosed. The process does not require preparation of samples or any cutting operations. The test equipment can be applied to the exterior surfaces of small enclosures or to the interior surfaces of large enclosures even if these latter are buried in the earth.

BRIEF DESCRIPTION OF THE DRAWING

FIG. 2 shows the time dependence of voltage by a plot of normalized parameters;

FIG. 6 is a typical plot of an oscilloscope trace of an operational measurement.

DESCRIPTION OF THE PREFERRED EMBODIMENT

If an electric current is suddenly forced to flow along one surface of a conductive sheet, electromagnetic fields are created which appose the spread of this current. Hence the current spreads, or diffuses, more or less slowly through the thickness of the sheet at a rate dependent upon the permeability and the resistivity of the sheet. The surface voltage gradient between two points on the sheet is a function of the magnitude of the current, the resistivity of the metal and the depth into the metal to which the current flow path has diffused at any particular instant.

Figure 1:
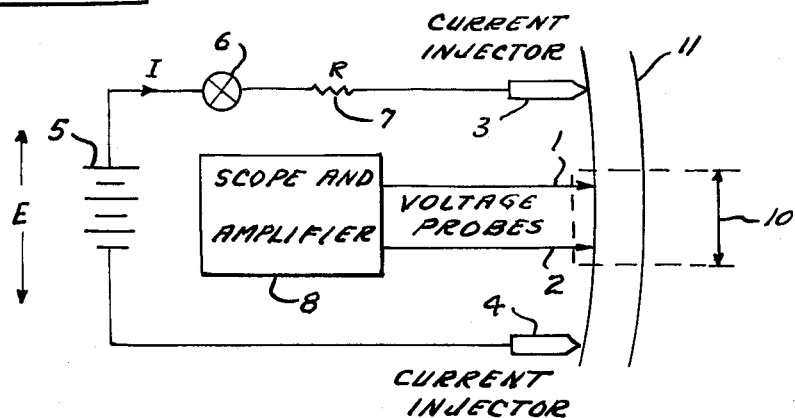
FIG. 1 is a simplified schematic diagram of an embodiment of the invention.

FIG. 1 is a simplified schematic diagram representative of the invention. When switch 6 is closed a steady current I will flow via the injectors 3 and 4 in sheet 11 after a few microseconds, provided that the voltage E from source 5 is constant and that resistance R of current limiting resistor 7 is sufficiently large to swamp the effects of any other impedances. This constant current will diffuse into the sheet until it flows uniformly throughout the thickness. The surface voltage gradient as sensed at probes 1 and 2, will thus decrease with time until the current flows uniformly throughout the thickness and steady state conditions are reached. By measuring the voltage time signature the electric and magnetic properties of the metal sheet 11 can be determined.

The magnetic field $H_o$ on the surface of metal sheet 11 central to the current injectors 3 and 4 as shown in FIG. 1 is $$H_o = \frac{1}{W} \quad (1)$$

where W is the effective width of the injectors including lateral spreading of the current. In the metal the field is governed by $$\frac{\delta H}{\delta \tau} = \rho \frac{\delta^2 H}{\delta X^2} \quad (2)$$

where X is the distance below the metal surface and the other quantities have their usual meaning. The voltage across the probes can be computed from $$V = \int_{\text{probe 1}}^{\text{probe 2}} E \cdot dl = \frac{d\phi}{d\tau} \text{ inside the boundary 10} \quad (3)$$

Thus $$V = l\rho \frac{\delta H}{\delta X}\bigg|_{x=0} \quad (4)$$

The solution (assuming constant $\mu$) gives $$V = \frac{\rho l H_o}{d}\left[1 - \frac{2}{\pi}\Sigma \exp\left(\frac{-n^2\pi^2\rho\tau}{\mu d^2}\right)\right] \quad (5)$$

For small values of time ($\tau$) the voltage goes as $1/\sqrt{\tau}$ and at late times V is constant. The conclusion of note as far as measurements are concerned is that only two sample peculiar parameters:

$$\frac{\rho}{d} \text{ and } \frac{\rho}{\mu d^2}$$

control the entire time history and therefore two relations between the three sample quantities can be obtained.

In the metal sheet at early times the current has not spread to the far wall so that the voltage measured on the near wall is the same as for an infinitely thick sheet. The boundary conditions are satisfied by functions of $X/\sqrt{\tau}$ in infinitely thick sheets of magnetic metal with nonlinear B - H properties when excited by step current pulses. Therefore $$H = f \frac{X}{\sqrt{\tau}}$$

From this equation and equation (4) we conclude that the measured voltage $$V = \frac{\rho l f'(o)}{\sqrt{\tau}}$$

and $f$ is the solution to $f'' + 2X\mu(f) f'^2 = 0$ which satisfies
$f = H_o$ at $X/\sqrt{\tau} = 0$
$f = 0$ at $X/\sqrt{\tau} \rightarrow \infty$ Thus equation (5) is not limited to cases of metal with constant $\mu$. The value of $\mu$ yielded by equation (5) for metals with nonlinear B — H properties, is an "effective" value which depends upon the details of the nonlinearity involved. FIG. 2 shows the time dependence of voltage by a plot 30 of normalized parameters from equation (5).

Equation (5) is not in a convenient form for use with test data. However, as seen in FIG. 2, a log-log plot of voltage versus time yields two straight lines. We term the early time history as "the (time) $^{-1/2}$ voltage decay phase" and the late time history as "the constant voltage phase", the intersection of these two straight lines defines the time T used below. Manipulation of equation (5) yields the following simple data reduction technique.

We define two parameters, measured from a plot of experimental results:

T, the time, after start of a pulse of constant current, at which the "(time) $^{-1/2}$ voltage decay phase" changes to the "constant voltage phase".

V, the voltage, between the two sensing contact points, during the "constant voltage phase".

The two quantities of interest which can be computed from the above measurements are:

$\rho$, the resistivity of the material under test.
$\mu_r$, the permeability of the material under test relative to the permeability of free space.

The equations used in these computations are:

$$\rho = \frac{KVdw}{Il} \quad (6)$$

$$\mu_r = \frac{KTVw}{4 \times 10^7 dIl} \quad (7)$$

Where:
$\rho$, (defined above), (measured in microhm — meters).
K, a constant dependent upon the geometric shape factors of the test head, determined empirically from measurement of known material.
V, (defined above), (measured in microvolts).
d, thickness of the sample (measured in inches).
w, width of the current injection contact fingers (measured in inches).
l, distance between the voltage sensing contact fingers (measured in inches).
I, magnitude of the current pulse (measured in amperes).
$\mu_r$, (defined above), (unitless constant).
T, (defined above), (measured in milliseconds).

Figure 3:
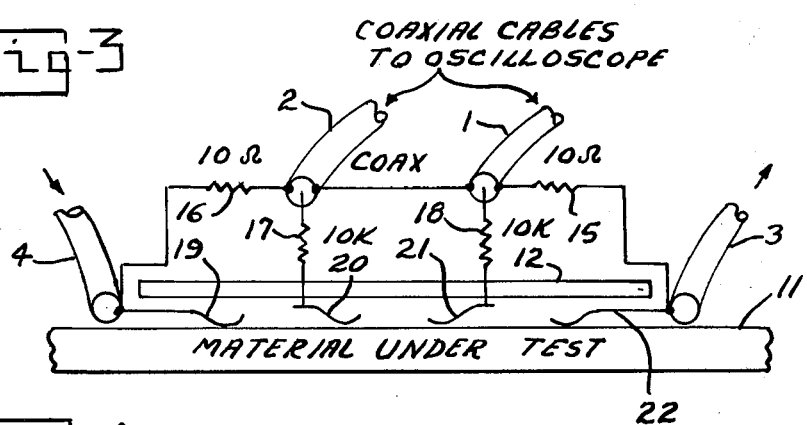
FIG. 3 is an elevation pictorial schematic diagram of a typical test fixture head.
Figure 4:
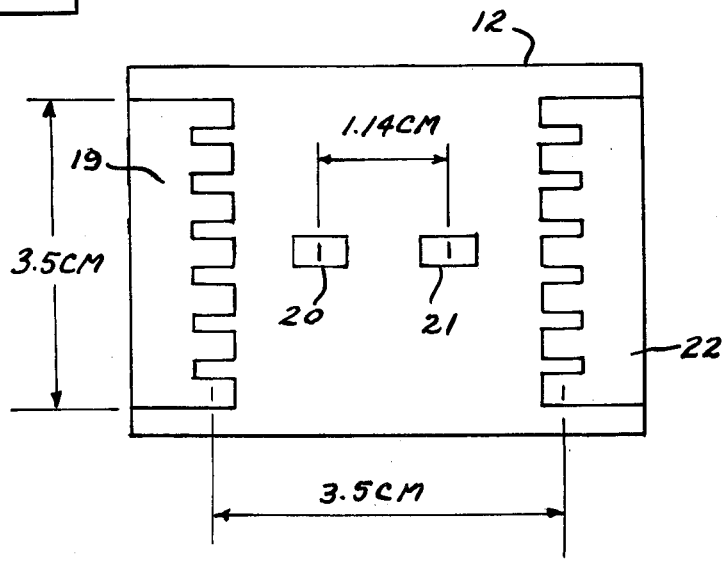
FIG. 4 is a plan view of the contact arrangement of the test head illustrated in FIG. 3.

FIGS. 3 and 4 show an operating embodiment of a typical Test Fixture Head which consists of four sets of spring contact fingers 19, 20, 21, and 22 designed to be pressed against a cleaned surface 11 of the material under test. A current (I) is injected into, and removed from, the surface using two rows of fingers 19 and 22 each 3.5 cm long separated by 3.5 cm. Two fingers, 20 and 21, spaced 1.14 cm apart, are used to measure the surface potential resulting from the flow of current I. To reduce problems of noise and interference a conventional differential amplifier is used to measure this signal. The 10,000 ohms resistors 17 and 18, together with the self-capacitance of the coaxial cables 1 and 2, filter out some high frequency noise. Common-mode signal is reduced by the use of the two 10 ohm resistors 15 and 16 which place "ground-potential" at approximately the mid-point potential to the material under test, thus causing most of the common-mode signal to be cancelled. The dimensions shown are typical and not critical.

Figure 5:
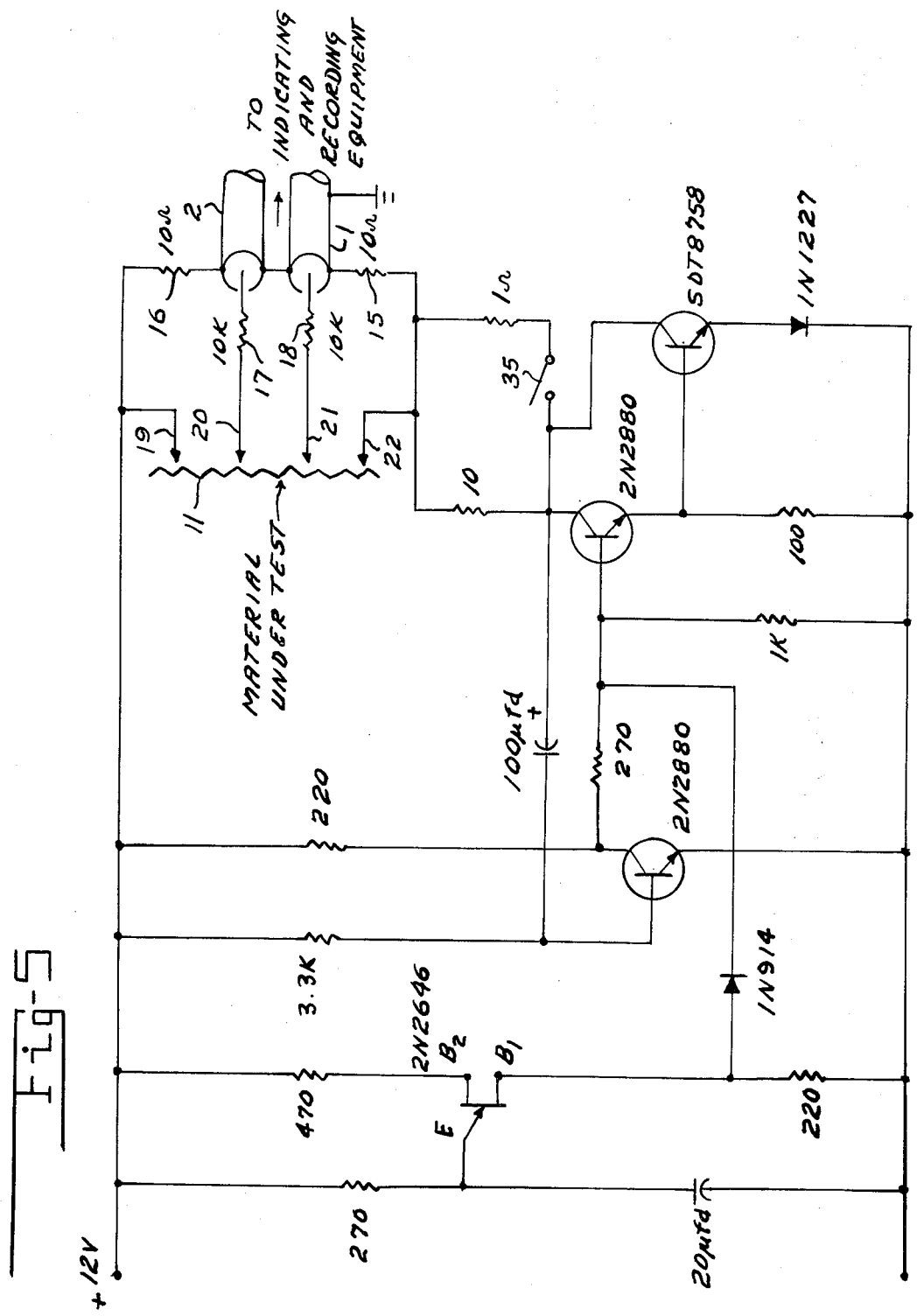
FIG. 5 is a representative schematic circuit of a typical drive circuit for supplying the step pulse.

FIG. 5 shows the circuit diagram of a typical drive circuit for generating the current step in the material. A SDT 8758 power transistor, together with a 2N2880 transistor form a Darlington pair, which when in the "on" condition allows either approximately 1 to 10 amps to flow through the material under test depending upon the position of switch 35. Feedback from this Darlington circuit through a second 2N2880 forms a monostable pulse generator which restricts the duration of the resulting current pulse to aprroximately 200 milliseconds. This current pulse is triggered approximately once every 10 seconds by a uni-junction relaxation oscillator using a 2N2646. The circuit is typically powered by a conventional rechargeable 12-volt battery.

With the typical test fixture head previously described, typical applied current densities are approximately 300 amps per meter width, at the 10.6 amp pulse level, and 30 amps per meter width, at the 1.03 amp pulse level. Typical measured signal responses ranged from 6200 micro-volts down to as low as 4.5 microvolts. The signal response rises rapidly, depending on the risetime of the constant current injection pulse, to a magnitude of several tens of millivolts. The signal then decays proportionately to (time) $^{-1/2}$ while the injected current diffuses through the thickness of the material under test. Thereafter the signal becomes constant at a magnitude dependent upon the resistivity of the material under test.

The most important factor affecting the accuracy of the test material is the calibration of the test head. That is the determination of the value of K in equations (6) and (7). This factor is dependent upon the geometric shape of the head and the resulting lateral current spreading in the surface plane of the material under test. This spreading reduces the current density per meter width injected into the surface of the material under test, below that value resulting from calculated values based on the physical width of the head. A typical value of K for the described test head has been found experimentally to be the value 1.62.

An embodiment of the invention as previously described has very satisfactorily been used to measure the components of resistance and permeability of the impedance of steel sheet and plate from approximately one-tenth inch to over one inch in thickness. As an example, FIG. 6 shows a plot 60 taken from an oscilloscope of the measurement of a steel plate 0.301 inch in thickness. Dotted lines 61 and 62 are extraporations of the straight line portions of the curve to show the point 63, the time after the onset of the current step pulse, at which voltage decay characteristic changes from a (time) $^{-1/2}$ function to a constant voltage phase function. This is the time T used in equation (7). From FIG. 6, the oscilloscope picture, for this particular plate, it can be seen that T has the value in milliseconds of approximately 18. From the curve it can also be seen that V the constant voltage is approximately 43 microvolts. Using the previously enumerated values, equations (6) and (7) may now be solved yielding a value of $\rho$ from equation (6) of 15.4 microhm-meters, and from equation (7) a value of $\mu_r$ of 119. It can readily be seen that since all the factors except V in equation (6) for determining the resistivity are constant for a given physical material the oscilloscope face can be calibrated so that $\rho$, the resistivity, may be read directly. In the particular measurement being described wherein $d$ the thickness of the plate is 0.301 inches, $\rho$ then equals 0.358 times V (with the previously described test head, having the stated parameters), where V is the microvolts of deflection. Also the value $\mu_r$ for this same measurement set-up is equal to .1535 times the product of 0.1535 time T (in milliseconds) to the constant voltage phase transitional point in the curve, and the value of V in the constant voltage phase (in microvolts), both values being easily read from the oscilloscope face.

Equations (6) and (7) may be simplified when a test head as previously described is used, to the following:

$$\rho = 1.19 \ Vd$$
$$\mu_r = 0.0462 \ \frac{TV}{d}$$

For 10.6 ampere pulse; and $$\rho = 12.2 \ Vd$$
$$\mu_r = 0.475 \ \frac{TV}{d}$$

For 1.03 ampere pulse

While the invention is primarily for obtaining characteristics of ferrous metals it is not limited thereto. The resistivities of materials such as copper plate, brass plate, and aluminum alloys have been satisfactorily determined with similar embodiments of the invention.

We claim:

1. A method of determining factors proportional to the resistivity and permeability of a sheet of ferrous material of known thickness comprising the steps of:
   a. passing a known current step from surface contacts through a determined length and width of the said sheet;
   b. displaying the voltage decay characteristics between surface contacts of a known separation located within the said determined length and width of the said surface contacts passing the said current step;
   c. observing in the said voltage decay characteristics the value in volts of the constant voltage phase of the said characteristic, and the value of time T in seconds at which the voltage decay characteristic changes from a (time) $^{-1/2}$ characteristic to a constant voltage phase characteristic, the said value in volts of the constant voltage phase being proportional to the said resistivity, and the product of the said value in volts and the said time T in seconds being proportional to the permeability of the said sheet.

* * * * *